US006371915B1

(12) United States Patent
Koger et al.

(10) Patent No.: US 6,371,915 B1
(45) Date of Patent: Apr. 16, 2002

(54) ONE-TWELFTH WAVELENGTH IMPEDENCE MATCHING TRANSFORMER

(75) Inventors: James D. Koger, Santa Cruz, CA (US); Robert W. Crowley, Sudbury, MA (US)

(73) Assignee: Scimed Life Systems, Inc., Maple Grove, MN (US)

( * ) Notice: Subject to any disclaimer, the term of this patent is extended or adjusted under 35 U.S.C. 154(b) by 0 days.

(21) Appl. No.: 09/432,914

(22) Filed: Nov. 2, 1999

(51) Int. Cl.[7] .................................................. A61B 8/00

(52) U.S. Cl. ....................... 600/445; 29/25.35; 310/336

(58) Field of Search ................................ 600/437, 445, 600/459; 73/642–644; 310/334–336; 29/25.35

(56) References Cited

U.S. PATENT DOCUMENTS

| | | | | | |
|---|---|---|---|---|---|
| 3,674,945 | A | | 7/1972 | Hands | 179/110 A |
| 4,205,686 | A | | 6/1980 | Harris et al. | 128/660 |
| 4,335,729 | A | | 6/1982 | Reynolds et al. | 128/674 |
| 4,348,904 | A | | 9/1982 | Bautista, Jr. | 73/644 |
| 4,366,406 | A | * | 12/1982 | Smith et al. | 73/632 |
| 4,523,122 | A | | 6/1985 | Tone et al. | 310/334 |
| 4,527,550 | A | | 7/1985 | Ruggera et al. | 128/1.5 |
| 4,594,897 | A | * | 6/1986 | Banty | 73/600 |
| 4,625,184 | A | | 11/1986 | Niitsuma et al. | 333/150 |
| 4,699,150 | A | | 10/1987 | Kawabuchi et al. | 128/660 |
| 4,756,808 | A | * | 7/1988 | Utsumi et al. | 204/180.2 |
| 4,795,935 | A | * | 1/1989 | Fujii et al. | 310/336 |
| 4,841,977 | A | | 6/1989 | Griffith et al. | 128/660 |
| 4,881,212 | A | * | 11/1989 | Takeuchi | 367/152 |
| 4,951,677 | A | | 8/1990 | Crowley et al. | 128/662 |
| 4,976,150 | A | * | 12/1990 | Deka | 73/644 |
| 5,291,090 | A | | 3/1994 | Dias | 310/334 |
| 5,386,395 | A | | 1/1995 | Le Guerinel et al. | 367/137 |
| 5,423,319 | A | | 6/1995 | Seyed-Bolorforosh | 128/663 |
| 5,434,827 | A | | 7/1995 | Bolorforosh | 367/140 |
| 5,438,997 | A | | 8/1995 | Sieben et al. | 128/662.06 |
| 5,445,155 | A | | 8/1995 | Sieben | 128/660 |
| 5,476,095 | A | | 12/1995 | Schnall et al. | 128/653 |
| 5,488,954 | A | | 2/1996 | Sleva et al. | 128/662.03 |
| 5,503,155 | A | | 4/1996 | Salmon et al. | 128/662.06 |
| 5,553,035 | A | | 9/1996 | Seyed-Bolorforosh et al. | 367/140 |
| 5,590,653 | A | | 1/1997 | Aida et al. | 128/653.2 |
| 5,634,939 | A | | 6/1997 | Kuster et al. | 607/59 |
| 5,699,801 | A | | 12/1997 | Atalar et al. | 128/653.2 |
| 5,779,644 | A | | 7/1998 | Eberle et al. | 600/463 |
| 6,014,898 | A | * | 1/2000 | Finsterwald et al. | 73/642 |

OTHER PUBLICATIONS

Try a Twelfth–Wave Transformer, Darrel Emerson, Jun. 1997, QST, vol. 81, No. 6.

* cited by examiner

*Primary Examiner*—Francis J. Jaworski
(74) *Attorney, Agent, or Firm*—Lyon & Lyon LLP

(57) ABSTRACT

An ultrasound transducer including a one-twelfth wavelength impedance matching transformer and methods of manufacturing and using the same. The transducer comprises a transducer element for transmitting and receiving ultrasound waves, a first impedance matching layer, and a second impedance matching layer. The transducer element has a transmitting/receiving surface, an impedance, and a thickness of substantially one-half wavelength of an ultrasound wave generated thereby. The first impedance matching layer is formed on the transmitting/receiving surface of the transducer element and has a thickness of substantially one-twelfth wavelength of the ultrasound wave travelling therein. The second impedance matching layer is formed on a selected surface of the first impedance matching layer and has a thickness of substantially one-twelfth wavelength of the ultrasound passing therethrough. An impedance of the first impedance matching layer is substantially equal to an impedance of an operating medium; whereas, an impedance of the second impedance matching layer is substantially equal to the impedance of the transducer element.

20 Claims, 4 Drawing Sheets

ONE-TWELFTH WAVELENGTH IMPEDENCE MATCHING TRANSFORMER

BACKGROUND OF THE INVENTION

1. Field of the Invention

The present invention relates generally to ultrasound imaging systems and, more particularly, to an ultrasound transducer including a one-twelfth wavelength impedance matching transformer and methods of manufacturing and using the same.

2. Background of the Invention

Intraluminal, intracavity, intravascular, and intracardiac treatment and diagnosis of medical conditions utilizing minimally invasive procedures is an effective tool in many areas of medical practice. These procedures typically are performed using imaging and treatment catheters that are inserted percutaneously into the body and into an accessible vessel, such as the femoral artery, of the vascular system at a site remote from a region of the body to be diagnosed and/or treated. The catheter then is advanced through the vessels of the vascular system to the region of the body to be diagnosed and/or treated, such as a vessel or an organ. The catheter may be equipped with an imaging device, typically an ultrasound imaging device, which is used to locate and diagnose a diseased portion of the body, such as a stenosed region of an artery.

Intravascular imaging systems having ultrasound imaging capabilities generally are known. For example, U.S. Pat. No. 4,951,677, issued to Crowley, the disclosure of which is incorporated herein by reference, describes such an intravascular ultrasound imaging system. An ultrasound imaging system typically contains some type of control system, a drive shaft, and a transducer assembly including an ultrasound transducer. The transducer assembly includes a transducer element and is coupled to the control system by the drive shaft. The drive shaft typically includes an electrical cable, such as coaxial cable, for providing electrical communication between the control system and the ultrasound transducer.

In operation, the drive shaft and the transducer assembly are inserted, usually within a catheter, into a patient's body and may be positioned near a remote region of interest. To provide diagnostic scans of the remote region of interest within, for example, a coronary blood vessel, the ultrasound transducer may be positioned near or within the remote region of the patient's body. Diagnostic scans are created when the control system alternately excites and allows sensing by the ultrasound transducer. The control system may direct the ultrasound transducer toward or away from an area of the remote region. When the ultrasound transducer is excited, a transmitting/receiving surface of the transducer element creates pressure waves in the bodily fluids surrounding the ultrasound transducer. The pressure waves then propagate through the fluids within the patent's body and ultimately reach the region of interest, forming reflected pressure waves. The reflected pressure waves then return through the fluids within the patient's body to the transmitting/receiving surface of the transducer element, inducing electrical signals within the transducer element. The control system then may collect the induced electrical signals and may reposition the ultrasound transducer to an adjacent area within the remote region of the patient's body, again exciting and sensing the transducer element. This process may continue until the remote region has been examined sufficiently and a series of induced signals has been collected. The control system then may process the series of induced signals to derive a diagnostic scan and may display a complete image of the diagnostic scan.

To create clear diagnostic scans, it is preferable that the ultrasound transducer have an impedance that is substantially equal to an impedance of the fluids within the patient's body, thereby maximizing the acoustic coupling between the ultrasound transducer and the patient's body. The technique of adding one or more one-quarter wavelength impedance matching layers to the transmitting/receiving surface of an ultrasound element generally is known. For example, U.S. Pat. No. 4,523,122, issued to Tone, the disclosure of which is incorporated herein by reference, describes the use of one-quarter wavelength acoustic impedance matching layers on piezoelectric ultrasound transducers. A one-quarter wavelength impedance matching layer provides an impedance transformation between the ultrasound transducer and an operating medium, for example, the fluids within a patient's body, to allow a better coupling of energy into the operating medium. The impedance transformation depends upon frequency, and the one-quarter wavelength impedance matching layers are used to compensate for the difference between the impedance of the ultrasound transducer and the impedance of the operating medium. The one-quarter wavelength impedance matching layer permits energy to be transmitted between the ultrasound transducer and the operating medium more efficiently, allowing a pressure wave produced by the ultrasound transducer to be introduced into the operating medium with less attenuation. The one-quarter wavelength matching layer also reduces the signal loss experienced when the reflected pressure wave returns from the operating medium and passes into the ultrasound transducer. Therefore, the use of the one-quarter wavelength impedance matching layers may provide for a stronger and sharper pressure wave and, thus, a better image.

However, the production of the one-quarter wavelength impedance matching layer currently poses several problems for ultrasound transducer manufacturers. First, materials with a proper matching impedance can be difficult to procure. Preferably, the impedance of the one-quarter wavelength impedance matching layer is determined substantially at the frequency of the ultrasound wave generated by the ultrasound transducer and is substantially equal to the geometric mean of the impedance of the transducer element and the impedance of the operating medium. Since the geometric mean calculation may result in a non-exact matching of impedances, finding proper materials for the impedance matching layer still may be difficult. Second, ultrasound transducer manufacturers may experience difficulty in uniformly disposing the one-quarter wavelength impedance matching layer on the transmitting/receiving surface of the transducer element. Due to the thickness of the one-quarter wavelength impedance matching layer, ultrasound transducer manufacturers may not be able to avail themselves of modem and more efficient manufacturing techniques, such as thin-film processing and deposition techniques, to produce ultrasound transducers with one-quarter wavelength impedance matching layers. These drawbacks and the limitation on available manufacturing techniques may result in ultrasound transducer manufacturers incurring additional costs that ultimately may be passed on to the patient.

A recent article, "Try a Twelfth-Wave Transformer," by Emerson, the disclosure of which is incorporated herein by reference, describes the use of a one-twelfth wavelength impedance matching transformer for coupling radio equipment to an antenna. The Emerson article suggests that coupling between an antenna cable and an antenna could be achieved by replacing a generally known one-quarter wavelength impedance matching transformer with a one-twelfth wavelength impedance matching transformer. The one-twelfth wavelength impedance matching transformer comprises a first impedance matching cable section and a second impedance matching cable section. The first impedance matching cable section has an impedance substantially equal to an impedance of the antenna and a length of substantially one-twelfth wavelength of a radio signal travelling therein. The second impedance matching cable section has an impedance substantially equal to an impedance of the antenna cable and a length of substantially one-twelfth wavelength of the radio signal passing therethrough. In operation, the first and second impedance matching sections are disposed between and couple the antenna cable and the antenna. The one-twelfth wavelength impedance matching transformer provides the advantages of broad bandwidth, a reduced overall length from one-quarter wavelength to one-sixth wavelength of the radio signal, and ready availability of cable sections to form the one-twelfth wavelength impedance matching transformer.

In view of the foregoing, it is believed that a need exists for an improved ultrasound transducer that overcomes the aforementioned obstacles and deficiencies of currently available ultrasound transducers.

SUMMARY OF THE INVENTION

The present invention is directed to an ultrasound transducer incorporating a one-twelfth wavelength impedance matching transformer for minimizing acoustic signal attenuation between a transducer element and an operating medium. The present invention provides the advantages of reduced physical size, enhanced diagnostic images, standardized impedance values, and decreased manufacturing costs.

In one preferred form, an ultrasound transducer in accordance with the present invention may comprise a transducer element for transmitting and receiving ultrasound waves, a first impedance matching layer, and a second impedance matching layer. The transducer element may be capable of generating an ultrasound wave with a preselected wavelength, may have a predetermined impedance, and may include a transmitting/receiving surface that is substantially flat. The transducer element preferably has a thickness substantially equal to one-half wavelength of the ultrasound wave generated thereby. The thickness of the transducer element may be substantially uniform.

The first impedance matching layer may have a thickness substantially equal to one-twelfth wavelength of the ultrasound wave travelling therein and, preferably, has an impedance substantially equal to an impedance of an operating medium, such as water or blood. The second impedance matching layer may have a thickness substantially equal to one-twelfth wavelength of the ultrasound wave passing therethrough and preferably has an impedance substantially equal to the impedance of the transducer element. Preferably, the first impedance matching layer is formed over a transmitting/receiving surface of the transducer element, and the second impedance matching layer is formed over an exterior surface of the first impedance matching layer. Stated somewhat differently, the first impedance matching layer may be deposited on the transmitting/receiving surface of the transducer element, and the second impedance matching layer may be deposited on the exterior surface of the first impedance matching layer.

The ultrasound transducer may also include a pair of electrodes, and the electrodes may be used to couple the ultrasound transducer to an ultrasound imaging system.

In a second preferred embodiment, the transducer element, the first impedance matching layer, and the second impedance matching layer each may be substantially concave in shape for reducing the focal length of the ultrasound transducer.

In a third preferred embodiment, the transducer element, the first impedance matching layer, and the second impedance matching layer each may be substantially convex in shape for increasing the focal length of the ultrasound transducer.

In a fourth preferred embodiment of the ultrasound transducer, the transducer element may include a backing layer. The backing layer may be attached to a back surface of the transducer element to absorb any energy radiating from the back surface of the transducer element. The backing layer preferably is formed from a high impedance material and acts to minimize image distortion resulting from reflections of undesired signals.

It will be appreciated that an ultrasound transducer incorporating a one-twelfth wavelength impedance matching transformer in accordance with the present invention may overcome the manufacturing problems associated with one-quarter wavelength impedance matching layers and enhance the quality of diagnostic images. First, by utilizing a one-twelfth wavelength impedance matching transformer, ultrasound transducer manufacturers may be able to utilize readily available materials. For example, since the first impedance matching layer may be formed from any hydroscopic material having an impedance similar to an impedance of water, ultrasound transducer manufacturers may choose from among a variety of commercial materials to produce the first impedance matching layer. The material for the second impedance matching layer also may be available to ultrasound transducer manufacturers because the second impedance matching layer may be formed from the same piezoelectric material that comprises the transducer element. Second, since each impedance matching layer on the ultrasound transducer has a thickness of only one-twelfth wavelength, more efficient manufacturing techniques, including thin-film processing and deposition techniques, may be used to produce the ultrasound transducer of the present invention. Enhanced diagnostic images are possible due to an increase in signal power transmitted between the ultrasound transducer and the operating medium as well as a reduction in internal reflections in the ultrasound transducer. It also will be appreciated that, by using more efficient manufacturing techniques, substantial savings in manufacturing costs may be passed on to patients required to undergo ultrasound imaging procedures, or to their insurers, through the use of matching transformers in accordance with the present invention.

DETAILED DESCRIPTION OF THE PREFERRED EMBODIMENTS

Figure 1:
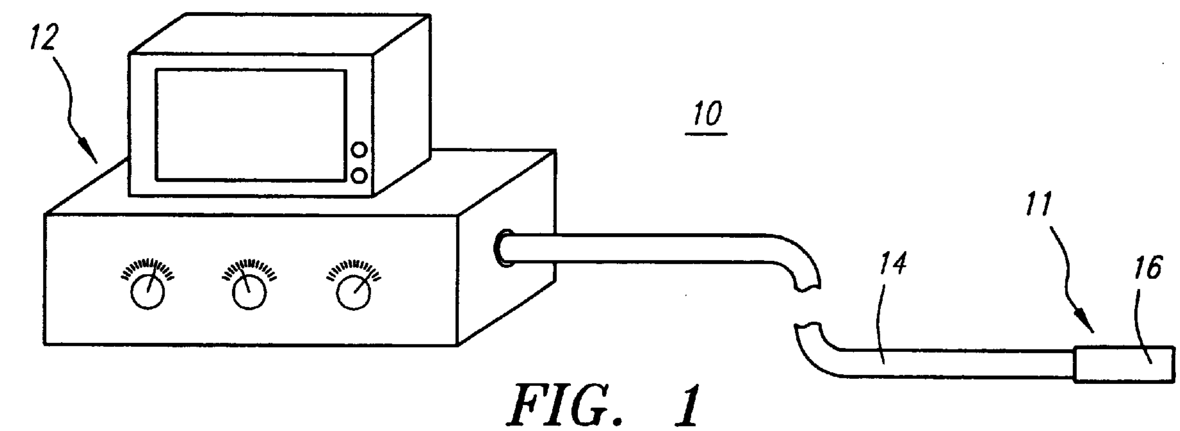
FIG. 1 (PRIOR ART)
FIG. 1 is an illustration of a typical prior art ultrasound imaging system.

Turning now to the drawings, FIG. 1 is an illustration of a typical ultrasound imaging system 10. The ultrasound imaging system 10 contains a control system 12, a drive shaft 14, and a sensor assembly 11 including an ultrasound transducer 16. The ultrasound transducer 16 may be coupled to the control system 12 by the drive shaft 14. The drive shaft 14 typically includes an electrical cable 15 (shown in FIG. 2A), such as coaxial cable, to provide electrical communication between the control system 12 and the ultrasound transducer 16.

Figure 2A:
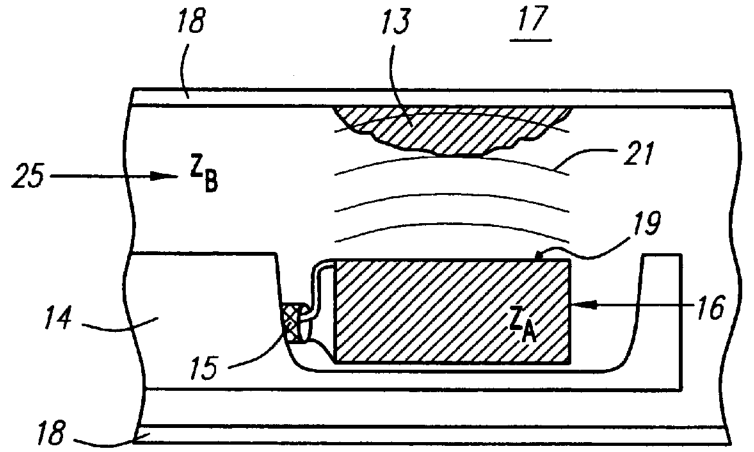
FIG. 2A (PRIOR ART)
FIG. 2A is a detailed view of a prior art ultrasound transducer in a transmitting mode.
Figure 2B:
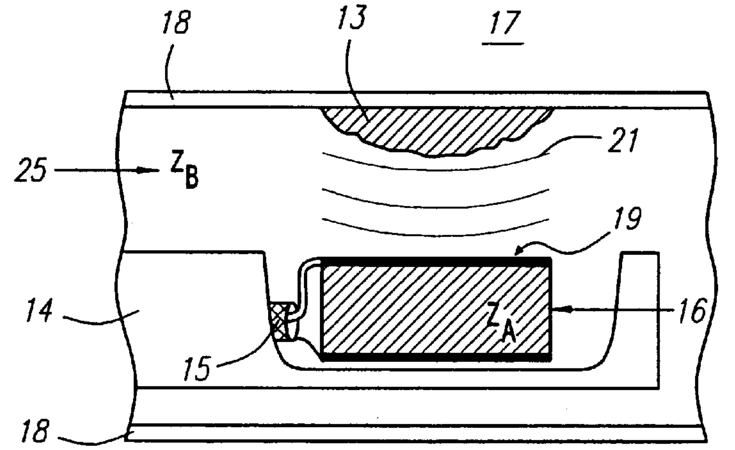
FIG. 2B (PRIOR ART)
FIG. 2B is a detailed view of a prior art ultrasound transducer in a receiving mode.

As shown in FIG. 2A, to provide diagnostic scans of a region of interest 13 within, for example, a blood vessel 18, the ultrasound transducer 16 may be positioned within a remote region 17 of a patient's body (not shown). Diagnostic scans are created when the control system 12 (shown in FIG. 1) alternately excites and allows sensing by the ultrasound transducer 16. When the ultrasound transducer 16 is excited, a transmitting/receiving surface 19 of the ultrasound transducer 16 creates pressure waves 21 in fluids 25 surrounding the ultrasound transducer 16 within the patient's body. The pressure waves 21 then propagate through the fluids 25 within patent's body to the region of interest 13. A portion of the pressure waves 21 reflect from the region of interest 13, forming reflected pressure waves 23, as shown in FIG. 2B. The reflected pressure waves 23 then return through the fluids 25 of the patient's body to the transmitting/receiving surface 19 of the ultrasound transducer 16 and induce electrical signals (not shown) within the ultrasound transducer 16. The control system 12 (shown in FIG. 1) then may collect the induced electrical signals and may adjust the drive shaft 14 to direct the ultrasound transducer 16 to an adjacent area (not shown) within the remote region 17 of the patient's body, again exciting and sensing the transducer element. This process may continue until the remote region 17 has been examined sufficiently and a series of induced signals has been collected. The control system 12 (shown in FIG. 1) then may process the series of induced signals to derive a diagnostic scan (not shown) and may display a complete image (not shown) of the diagnostic scan.

To create clear diagnostic scans, it is preferable that the ultrasound transducer 16 be sufficiently small to travel safely to the remote region 17 through narrow blood vessels 18 or other cavities within the patient's body without dangerously restricting blood flow or other body functions. The ultrasound transducer 16 also preferably has an impedance $Z_A$ that is substantially equal to an impedance $Z_B$ of the fluids 25 in the patient's body to maximize the acoustic coupling between the ultrasound transducer 16 and the fluids 25.

Figure 3:
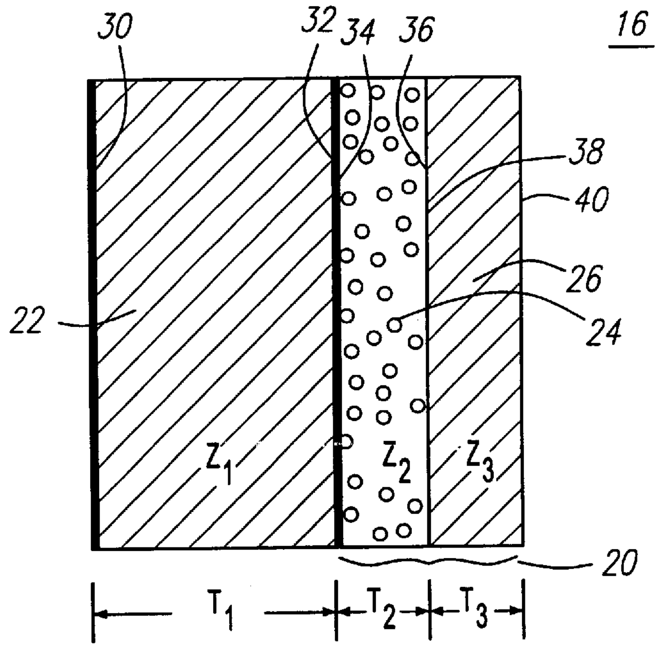
FIG. 3 is an illustration of one preferred embodiment of an ultrasound transducer for internal imaging systems in accordance with the present invention.

These requirements may be achieved, according to one embodiment of the present invention, by employing an ultrasound transducer 16 that includes a one-twelfth wavelength impedance matching transformer 20, as shown in FIG. 3. The ultrasound transducer 16 of the present invention preferably comprises a transducer element 22 for transmitting and receiving ultrasound waves, a first impedance matching layer 24, and a second impedance matching layer 26. The transducer element 22 preferably has an impedance $Z_1$, a transmitting/receiving surface 32, and a thickness $T_1$, of substantially one-half wavelength of ultrasound waves generated by the transducer element 22. The transmitting/receiving surface 32 of the transducer element 22 may be substantially flat, and the thickness $T_1$of the transducer element 22 preferably is substantially uniform.

The first impedance matching layer 24 may have a back surface 34 and a front surface 36, and the back surface 34 of the first impedance matching layer 24 may communicate with the transmitting/receiving surface 32 of the transducer element 22. The first impedance matching layer 24 also may have an impedance $Z_2$ and a thickness $T_2$. Preferably, the impedance $Z_2$ of the first impedance matching layer 24 is substantially equal to an impedance of an operating medium, such as water or blood, within which the ultrasound transducer 16 is used. The thickness $T_2$ of the first impedance matching layer 24 preferably is substantially one-twelfth wavelength of the ultrasound waves travelling therein. The back surface 34 and the front surface 36 of the first impedance matching layer 24 each may be substantially flat, and the thickness $T_2$ of the first impedance matching layer 24 preferably is substantially uniform.

The second impedance matching layer 26 may have a back surface 38 and a sensing surface 40, and the back surface 38 of the second impedance matching layer 26 may communicate with the front surface 36 of the first impedance matching layer 24. The second impedance matching layer 26 also may have an impedance $Z_3$ and a thickness $T_3$. Preferably, the impedance $Z_3$ of the second impedance matching layer 26 is substantially equal to the impedance $Z_1$, of the transducer element 22. The thickness $T_3$ of the second impedance matching layer 26 preferably is substantially equal to one-twelfth wavelength of the ultrasound waves passing therethrough. The back surface 38 and the sensing surface 40 of the second impedance matching layer 26 each may be substantially flat, and the thickness $T_3$ of the second impedance matching layer 26 preferably is substantially uniform.

The transducer element 22 preferably is formed from a piezoelectric material; whereas, the first impedance matching layer 24 and the second impedance matching layer 26 may be formed from virtually any material having the respective desired impedances. The impedance $Z_2$ of the first impedance matching layer 24 preferably is approximately equal to an impedance of an operating medium, such as water or blood, within which the ultrasound transducer 16 is used. The first impedance matching layer 24 may be formed from a hydroscopic material. The hydroscopic material may include, for example, an aerogel, a hydrogel, water, or any other hydroscopic or permeable substance. Those skilled in the art will understand that, where an aerogel is used, the impedance $Z_1$ of the transducer element 22 alternatively may be matched to an impedance of air. Preferably, the impedance $Z_3$ of the second impedance matching layer 26 is approximately equal to the impedance $Z_1$, of the transducer element 22. The second impedance matching layer 26 may be formed from a piezoelectric material. The piezoelectric material may include, for example, PZT (Lead Zirconate Titanate) type ceramic material, or any other piezoelectric material. Very preferably, the second impedance matching layer 26 is formed form the piezoelectric material that comprises the transducer element 22.

The wavelength of an ultrasound wave may vary depending upon the type of medium within which the ultrasound wave travels. Within the one-twelfth wavelength impedance matching transformer 20, the first impedance matching layer 24 may differ in composition from the second impedance matching layer 26. The wavelength of the ultrasound waves travelling within the first impedance matching layer 24 may therefore differ from the wavelength of the ultrasound waves passing through the second impedance matching layer 26. Thus, since the thickness $T_2$ of the first impedance matching layer 24 and the thickness $T_3$ of the second impedance matching layer 26 each depend upon the wavelength of the ultrasound wave passing through the respective layers, the thickness $T_2$ of the first impedance matching layer 24 may differ from the thickness $T_3$ of the second impedance matching layer 26.

Figure 4:
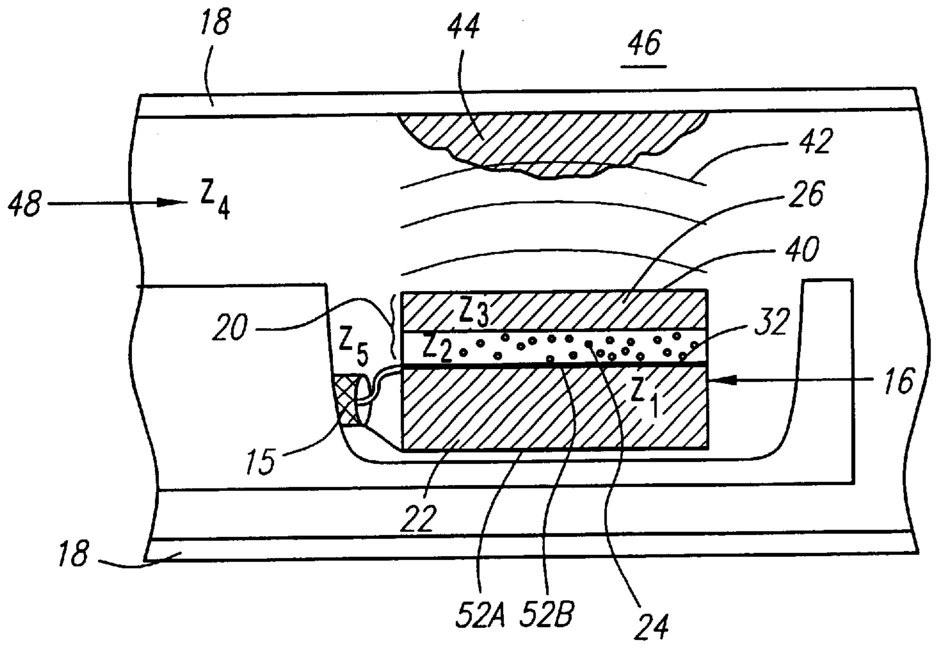
FIG. 4 is a detailed view of the ultrasound transducer of FIG. 3 when operated in a transmitting mode.

As shown in FIG. 4, the transducer element 22 may include a pair of electrodes 52*a* and 52*b* for coupling the ultrasound transducer 16 with the electrical cable 15 within the drive shaft 14 of the ultrasound imaging system 10 (shown in FIG. 1). The transducer element 22 may, for example, be directly coupled to the electrical cable 15, as shown in FIG. 4. Very preferably, an impedance $Z_5$ of the electrical cable 15 is substantially equal to the impedance $Z_1$, of the transducer element 22.

Thus, the ultrasound transducer 16 of the present invention may be coupled to the control system 12 (shown in FIG. 1) of the ultrasound imaging system 10 (shown in FIG. 1) by an electrical cable 15. The ultrasound transducer 16 then may be positioned near a region of interest 44 within a remote region 46 of the patient's body, providing diagnostic scans of, for example, a blood vessel wall 18. Preferably, the impedance $Z_2$ of the first impedance matching layer 24 is substantially equal to an impedance $Z_4$ of fluids 48 surrounding the ultrasound transducer 16 within the patient's body, and the impedance $Z_3$ of the second impedance matching layer 26 is substantially equal to the impedance $Z_1$, of the transducer element 22.

In operation, when the ultrasound transducer 16 is excited, the transducer element 22 may transmit pressure waves 42. The pressure waves 42 may exit the transducer element 22 through the transmitting/receiving surface 32 and may propagate through the matching transformer 20. The pressure waves may exit the ultrasound transducer 16 from the sensing surface 40 of the second impedance matching layer 26. The pressure waves 42 then enter the fluids 48 within the patient's body. Since the impedance matching transformer 20 may improve the coupling between the ultrasound transducer 16 and the fluids 48 within the patient's body, the pressure waves 42 may be stronger and sharper within the fluids 48.

Figure 5:
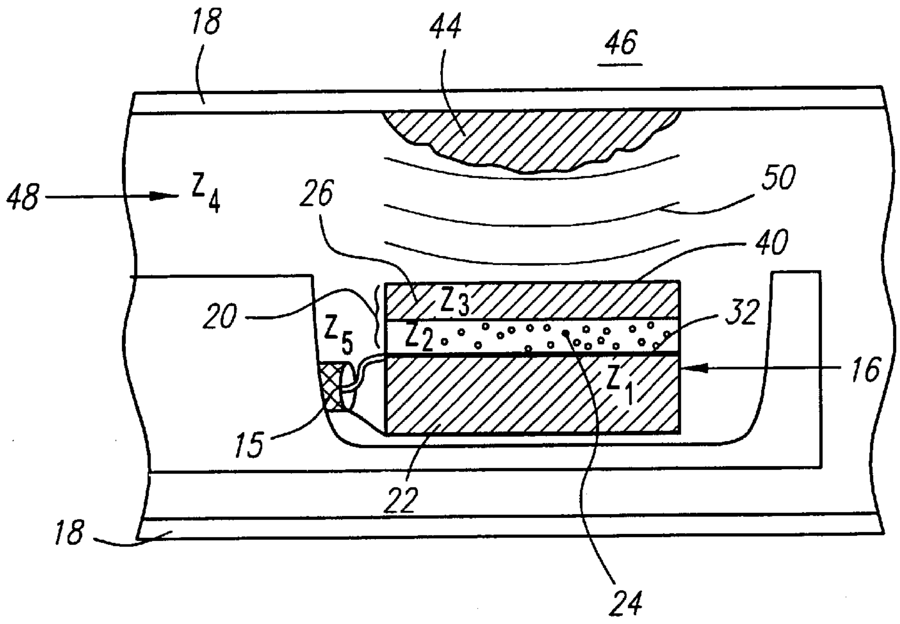
FIG. 5 is a detailed view of the ultrasound transducer of FIG. 3 when operated in a receiving mode.

When the pressure waves 42 reach the region of interest 44, reflected pressure waves 50 may be formed, as shown in FIG. 5. The reflected pressure waves 50 may return through the fluids 48 within the patient's body to the ultrasound transducer 16. The reflected pressure waves 50 may enter the sensing surface 40 of the second impedance matching layer 26 and may propagate through the matching transformer 20, reaching the transmitting/receiving surface 32 of the transducer element 22. The reflected pressure waves 50 may pass through the transmitting/receiving surface 32 and may enter the transducer element 22. Since the impedance matching transformer 20 may reduce internal reflections and improve the coupling between the ultrasound transducer 16 and the fluids 48 within the patient's body, the reflected pressure waves 50 may propagate into the transducer element 22 with less attenuation and distortion. Within the transducer element 22, the reflected pressure waves 50 may excite the transducer element 22, creating electrical signals. The control system 12 (shown in FIG. 1) then may sense and process the induced electrical signals to develop a diagnostic scan (not shown) and display a complete image (not shown) of the diagnostic scan. Thus, the complete image may more accurately represent the region of interest 44 because the pressure waves 42 and the reflected pressure waves 50 may have experienced less attenuation and distortion when passing between the transducer element 22 and the fluids 48 within the patient's body.

Figure 6:
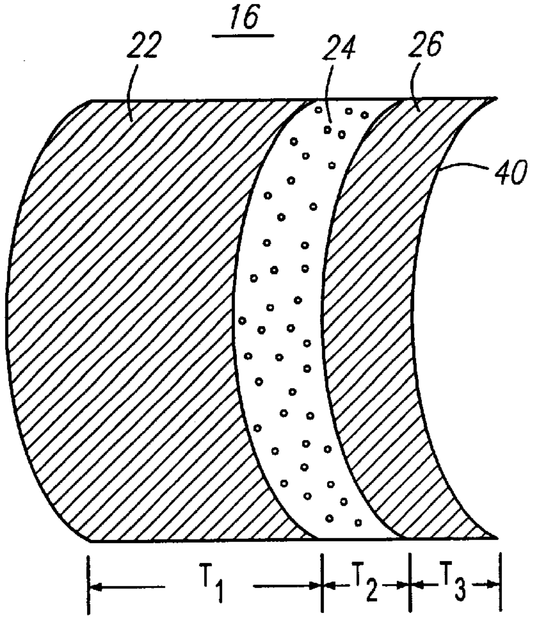
FIG. 6 is an illustration of a second preferred embodiment of an ultrasound transducer in accordance with the present invention.
Figure 7:
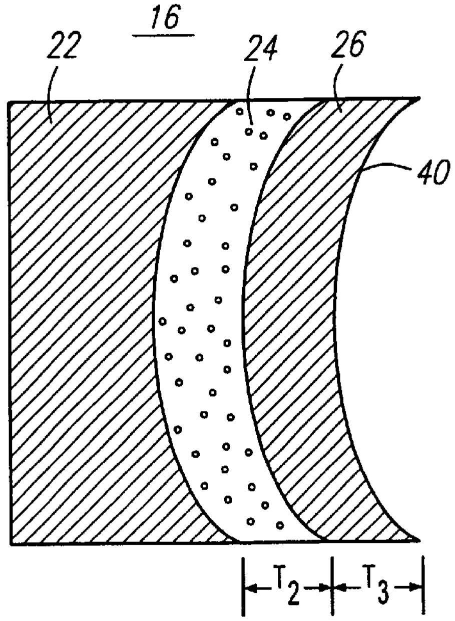
FIG. 7 is an illustration of an alternative construction of the ultrasound transducer shown in FIG. 6.

In a second preferred embodiment, the sensing surface 40 of the second impedance matching layer 26 may comprise a substantially concave surface for reducing a focal length (not shown) of the ultrasound transducer 16. The first impedance matching layer 24, the second impedance matching layer 26, and the transducer element 22 each preferably is substantially concave in shape, as shown in FIG. 6. The thickness $T_2$ of the first impedance matching layer 24 may be substantially uniform, and the thickness $T_3$ of the second impedance matching layer 26 may be substantially uniform. The thickness $T_1$, of the transducer element 22 preferably is substantially uniform. Alternatively, the transducer element 22 may have a substantially flat back surface 30, as shown in FIG. 7.

Figure 8:
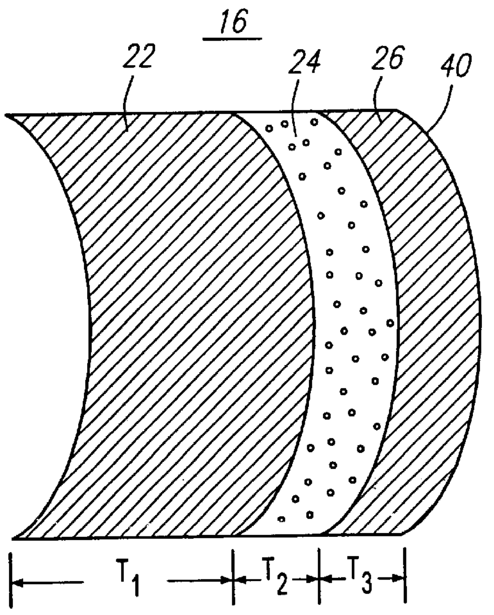
FIG. 8 is an illustration of a third preferred embodiment of an ultrasound transducer in accordance with the present invention.
Figure 9:
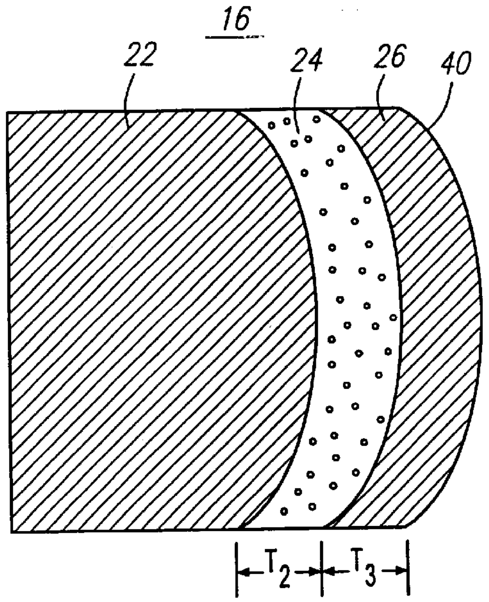
FIG. 9 is an illustration of an alternative construction of the ultrasound transducer shown in FIG. 8.

In a third preferred embodiment, the sensing surface 40 of the second impedance matching layer 26 may comprise a substantially convex surface for increasing the focal length of the ultrasound transducer 16. In such an embodiment, the first impedance matching layer 24, the second impedance matching layer 26, and the transducer element 22 each preferably are substantially convex in shape, as shown in FIG. 8. The thickness $T_2$ of the first impedance matching layer 24 may be substantially uniform, and the thickness $T_3$ of the second impedance matching layer 26 may be substantially uniform. Similarly, the thickness $T_1$, of the transducer element 22 preferably is substantially uniform. The back surface 30 of the transducer element 22 alternatively may be substantially flat, as shown in FIG. 9.

Figure 10:
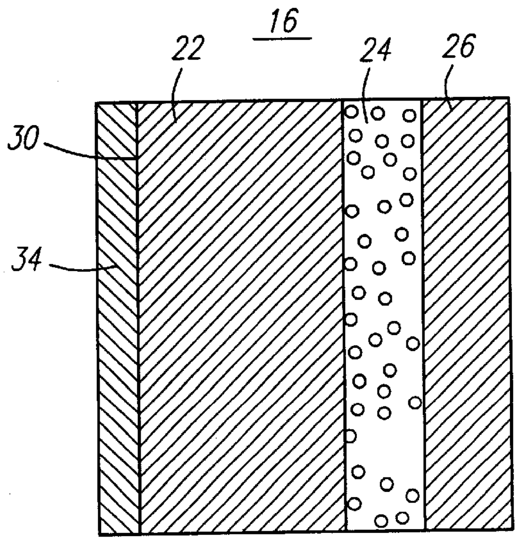
FIG. 10 is an illustration of a fourth preferred embodiment of an ultrasound transducer in accordance with the present invention.

In a fourth preferred embodiment, the transducer element 22 may include a backing layer 34 for absorbing energy radiating from the back surface 30 of the transducer element 22, as shown in FIG. 10. The backing layer 34 preferably acts to minimize image distortion resulting from reflections of undesired signals (not shown) and may be formed from a high impedance material.

The ultrasound transducer 16 with the one-twelfth wavelength impedance matching transformer 20 of the present invention may overcome the manufacturing problems associated with a one-quarter wavelength impedance matching layer (not shown). First, by utilizing the one-twelfth wavelength impedance matching transformer 20, ultrasound transducer manufacturers may have access to a broader selection of materials. Preferably, the first impedance matching layer 24 and the second impedance matching layer 26 each have a standard impedance and are formed from readily available materials. Since the first impedance matching layer 24 may be formed from any hydroscopic material having an impedance similar to an impedance of water, ultrasound transducer manufacturers may choose from among a variety of materials to produce the first impedance matching layer 24. The material for the second impedance matching layer 26 also may be available to ultrasound transducer manufacturers because the second impedance matching layer 26 may be formed from the same piezoelectric material that comprises the transducer element 22. Second, since the first impedance matching layer 24 and the second impedance matching layer 26 each are much thinner than the one-quarter wavelength impedance matching layers, ultrasound transducer manufacturers may employ more efficient manufacturing techniques, such as thin-film processing and deposition techniques, to produce the one-twelfth wavelength impedance matching transformer 20.

While the invention is susceptible to various modifications and alternative forms, specific examples thereof have been shown by way of example in the drawings and are herein described in detail. It should be understood, however, that the invention is not to be limited to the particular forms or methods disclosed, but to the contrary, the invention is to cover all modifications, equivalents, and alternatives falling within the spirit and scope of the appended claims.

What is claimed is:

1. An ultrasound transducer comprising:

a transducer element for transmitting and receiving ultrasound waves, said transducer element having an impedance and a transmitting/receiving surface, and said transducer element being capable of generating an ultrasound wave having a preselected wavelength;

a first impedance matching layer, said first impedance matching layer having a front surface, a back surface in communication with said transmitting/receiving surface of said transducer element, an impedance substantially equal to an impedance of an operating medium, and a first thickness of substantially one-twelfth wavelength of said ultrasound wave within said first impedance matching layer; and a second impedance matching layer, said second impedance matching layer having a back surface in communication with said front surface of said first impedance matching layer, an impedance substantially equal to said impedance of said transducer element, and a second thickness of substantially one-twelfth wavelength of said ultrasound wave within said second impedance matching layer.

2. The ultrasound transducer of claim 1, wherein said impedance of said first impedance matching layer is substantially equal to an impedance of water.

3. The ultrasound transducer of claim 1, wherein said impedance of said first impedance matching layer is substantially equal to an impedance of blood.

4. The ultrasound transducer of claim 1, wherein said thickness of said transducer element is substantially equal to one-half wavelength of said ultrasound wave generated therein.

5. The ultrasound transducer of claim 1, further comprising a backing layer for absorbing energy radiating from a back surface of said transducer element, said backing layer coupled to said back surface of said transducer element.

6. The ultrasound transducer of claim 5, wherein said backing layer is formed from a high impedance material.

7. The ultrasound transducer of claim 1, wherein said first impedance matching layer, said second impedance matching layer, and said transducer element each are substantially flat.

8. The ultrasound transducer of claim 1, wherein said transducer element, said first impedance matching layer, and said second impedance matching layer each are substantially concave.

9. The ultrasound transducer of claim 1, wherein said transducer element, said first impedance matching layer, and said second impedance matching layer each are substantially convex.

10. The ultrasound transducer of claim 1, wherein said transducer element is formed from a first piezoelectric material, and said second impedance matching layer is formed from a second piezoelectric material.

11. The ultrasound transducer of claim 10, wherein said first piezoelectric material comprises a PZT (Lead Zirconate Titanate) type ceramic material.

12. The ultrasound transducer of claim 10, wherein said second impedance matching layer comprises a PZT (Lead Zirconate Titanate) type ceramic material.

13. The ultrasound transducer of claim 1, wherein said first matching layer is formed from a substantially hydroscopic material.

14. The ultrasound transducer of claim 1, wherein said first matching layer is formed from a substantially permeable material.

15. The ultrasound transducer of claim 1, wherein said first matching layer substantially comprises water.

16. The ultrasound transducer of claim 1, wherein said first matching layer substantially comprises a hydrogel.

17. The ultrasound transducer of claim 1, wherein said first matching layer substantially comprises an aerogel.

18. An ultrasound transducer comprising:

a transducer element for transmitting and receiving ultrasound waves, said transducer element being capable of generating an ultrasound wave with a preselected wavelength, said transducer element having an impedance, a transmitting/receiving surface, a back surface, a pair of electrodes for communicating with an imaging system, and a thickness of substantially one-half wavelength of said ultrasound wave generated therein;

a first impedance matching layer, said first impedance matching layer having a front surface, a back surface coupled to said transmitting/receiving surface of said transducer element, an impedance substantially equal to an impedance of an operating medium, and a first thickness of substantially one-twelfth wavelength of said ultrasound wave when travelling therein;

a second impedance matching layer, said second impedance matching layer having a back surface coupled to said front surface of said first impedance matching layer, an impedance substantially equal to said impedance of said transducer element, and a second thickness of substantially one-twelfth wavelength of said ultrasound wave when travelling therein; and a backing layer for absorbing energy radiating from said back surface of said transducer element, said backing layer being formed from a reflection minimizing material and coupled to said back surface of said transducer element.

19. A system for deriving diagnostic images comprising:

a control system for exciting and sensing an ultrasound transducer;

a drive shaft, said drive shaft having a first end coupled to said control system and a second end;

an ultrasound transducer for transmitting and receiving ultrasound waves, said ultrasound transducer coupled to said second end of said drive shaft and comprising a transducer element, a first impedance matching layer, and a second impedance matching layer;

said transducer element being capable of generating an ultrasound wave with a preselected wavelength and having an impedance, a transmitting/receiving surface, and a thickness of substantially one-half wavelength of said ultrasound wave generated therein;

said first impedance matching layer having a front surface, a back surface coupled to said transmitting/receiving surface of said transducer element, an impedance substantially equal to an impedance of an operating medium, and a first thickness of substantially one-twelfth wavelength of said ultrasound wave travelling therein; and said second impedance matching layer having a back surface coupled to said front surface of said first impedance matching layer, an impedance substantially equal to said impedance of said transducer element, and a second thickness of substantially one-twelfth wavelength of said ultrasound wave travelling therein.

20. A method of manufacturing an ultrasound transducer, said method comprising the steps of:

providing a transducer element for transmitting and receiving ultrasound waves, said transducer element being capable of generating an ultrasound wave with a preselected wavelength and having an impedance, a transmitting/receiving surface, and a thickness of substantially one-half wavelength of said ultrasound wave generated therein;

forming a first impedance matching layer on said transmitting/receiving surface of said transducer element, said first impedance matching layer having an impedance substantially equal to an impedance of an operating medium and a first thickness of substantially one-twelfth wavelength of said ultrasound wave travelling therein; and forming a second impedance matching layer on a selected surface of said first impedance matching layer, said second impedance matching layer having an impedance substantially equal to said impedance of said transducer element and a second thickness of substantially one-twelfth wavelength of said ultrasound wave travelling therein.

* * * * *

UNITED STATES PATENT AND TRADEMARK OFFICE

CERTIFICATE OF CORRECTION

PATENT NO. : 6,371,915 B1 
DATED : April 16, 2002
INVENTOR(S) : James D. Koger and Robert J. Crowley It is certified that error appears in the above-identified patent and that said Letters Patent is hereby corrected as shown below:

Title page,
Item [75], Inventors, please change "Robert W. Crowley" to
-- Robert J. Crowley --.

Signed and Sealed this

Eighteenth Day of February, 2003

JAMES E. ROGAN
*Director of the United States Patent and Trademark Office*